United States Patent
Chen et al.

(10) Patent No.: US 8,538,511 B2
(45) Date of Patent: Sep. 17, 2013

(54) APPARATUS FOR COLLECTING A PHYSIOLOGICAL SIGNAL

(75) Inventors: Jeng-Chung Chen, Taipei County (TW);
Terry B. J. Kuo, Taipei (TW)

(73) Assignee: Vicon Healthcare International Inc., Taipei (TW)

( * ) Notice: Subject to any disclaimer, the term of this patent is extended or adjusted under 35 U.S.C. 154(b) by 0 days.

(21) Appl. No.: 13/451,218

(22) Filed: Apr. 19, 2012

(65) Prior Publication Data

US 2013/0172766 A1   Jul. 4, 2013

(30) Foreign Application Priority Data

Jan. 4, 2012   (TW) .............................. 101200170 A

(51) Int. Cl.
*A61B 5/04* (2006.01)
(52) U.S. Cl.
USPC ........................................................ 600/519
(58) Field of Classification Search
USPC ................. 600/519, 301, 302, 481, 502, 509, 600/515
See application file for complete search history.

(56) References Cited

U.S. PATENT DOCUMENTS

| | | | |
|---|---|---|---|
| 2007/0149888 A1* | 6/2007 | Kohls et al. ................... | 600/509 |
| 2007/0276261 A1* | 11/2007 | Banet et al. ................... | 600/481 |
| 2008/0077027 A1* | 3/2008 | Allgeyer ........................ | 600/509 |
| 2008/0294058 A1* | 11/2008 | Shklarski ....................... | 600/502 |
| 2011/0028821 A1* | 2/2011 | Bojovic et al. ................ | 600/382 |
| 2011/0066010 A1* | 3/2011 | Moon et al. ................... | 600/301 |
| 2011/0301439 A1* | 12/2011 | Albert et al. .................. | 600/301 |
| 2011/0306894 A1* | 12/2011 | Spaulding et al. ............ | 600/515 |
| 2012/0016210 A1* | 1/2012 | Kim et al. ..................... | 600/301 |

* cited by examiner

*Primary Examiner* — George Manuel
*Assistant Examiner* — Robert N Wieland
(74) *Attorney, Agent, or Firm* — WPAT, P.C.; Anthony King

(57) ABSTRACT

The present invention relates to an improved apparatus for collecting a physiological signal, comprising a main body, including two devices for taking out the physiological signal from a finger at each side of the main body by pressing the finger therein, each device for taking out the physiological signal from a finger including: a finger contacting element, provided thereon an electrode unit for taking out an electronic signal of the physiological signal at the time of being contacted by the finger; a receiving element, provided on an upper side of the finger contacting element; and an elastic element, being connected to the receiving element, wherein each elastic element is opened an angle at each receiving element according to elastic force of each elastic element, and each finger inserts into a space and engages with the finger contacting element and the receiving element.

11 Claims, 2 Drawing Sheets

APPARATUS FOR COLLECTING A PHYSIOLOGICAL SIGNAL

FIELD OF THE INVENTION

The present invention is related to an improved apparatus for collecting a physiological signal.

DESCRIPTION OF PRIOR ART

In the current tendency of medical electronics, consideration of modern medical thinking has moved from taking care in a hospital end toward satisfying with the patient end, i.e. emphasizing problem solving orientation centered with the patient. Currently, the medical expenditure of the developed countries has been enormous. In order to decrease the medical expenditure and promote independent living thinking of the patient. Thus, it is tended to develop "Patient Enabling Technology". As such, the medical care products for in-home use are developed to become miniaturized to facilitate carrying. Additionally, expect for the above factors and progress of the current information technology and the network technology, a concept of Health 2.0, provided with a platform for estimating health information is forming gradually, i.e. directing to a design of a network cloud platform for providing information service to conditions of a human, which also converts the concept of health care from measuring by an individual himself to setting the health target and promoting health with the aid of the information provided by the platform.

The "Autonomic Nerves System" is quite complex system in the human body, which is closely linked to daily operation of the human. For example, systems of heartbeat, blood pressure, respiration, mediation of body temperature, gastrointestinal peristalsis and excretory function are associated with autonomic nerves system. The autonomic nerves system mainly divides into sympathetic nervous system and parasympathetic nervous system. The two systems are antagonized mutually and maintain a reasonable operation of the function of the important organs of the body. They serve like a throttle and a brake in operation. When the body meets with a condition under pressure, the sympathetic nervous system will be excited to produce enough response for the body to resist the pressure, and vice versa. On the other hand, in a certain condition that the sympathetic nervous continues to be excited, peripheral vascular continues to contract to cause poor peripheral circulation, while causing metabolic disturbance, which will cause syndrome, such as, shoulders ache or muscle ache etc.; however, when the parasympathetic nervous continues to be excited and the muscle of a bronchus contracts, it will cause a syndrome like dyspnea or asthma. In summary, if the autonomic nerve is abnormal, the performance ability for living is decreased. It will affect cerebral cortex and limbic system, resulting in various acute and chronic diseases, such as uneasy, decreased desire, decreased concentration, heart disease and hypertension, the serious patient even induces a sudden death. Thus, in medical science, it is becoming a more important issue for the health care of the autonomic nerves system.

Heart rate variability is a method for measuring continuous variation degree of heartbeat rate. The method mainly uses a calculation method of analyzing time sequence between heartbeats measured by an electrocardiogram or pulse measured. Except auto-rhythmicity, the heart is also regulated by the autonomic nervous system (ANS). In the past 20 years, many literatures have disclosed the outstanding relationship in regulation of the autonomic nerves system and the death rate of related cardiovascular diseases, for example, sudden cardiac death, hypertension, hemorrhagic shock and septic shock etc.

In the past, when the user measured heart rate variability, the electrode pastes must be stuck to and pasted on the suitable location, such as, arms of two hands or a front of chest. However, it is inconvenient to storage and carry for the user. In addition, the electrode pastes are exposed in the air in a long-time, they will subject to contamination easily and need to be replaced frequently.

In addition, there are many HRV machines to measure heart rate variability via pressing by fingers; however, the results of measurement are not accurate due to the design of the HRV machine needs to press by self for 5 minutes during measuring and after long-time pressing, it cause finger ache, and the finger move frequently. Furthermore, the finger does not press precisely, the machine even cannot measure a physiological signal.

Therefore, it is desirable to provide an improved apparatus for collecting a physiological signal to overcome the above-said problems.

SUMMARY OF THE INVENTION

Figure 1:
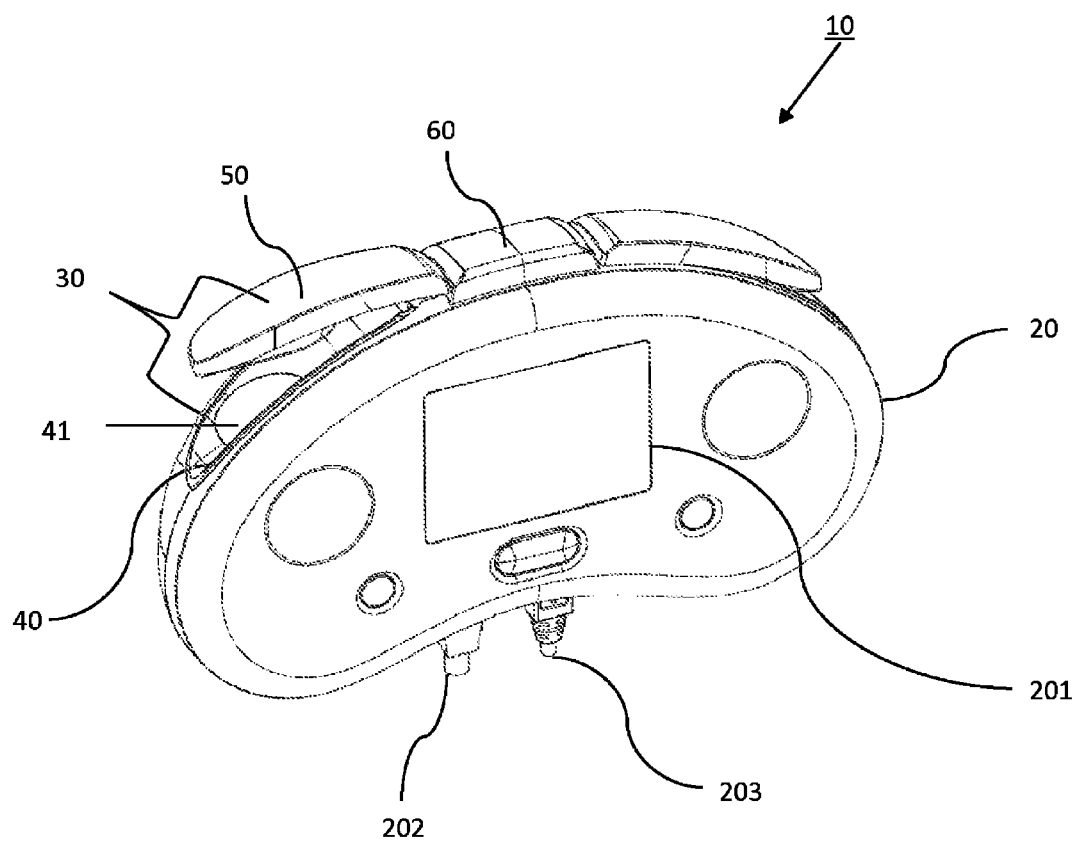
FIG. 1 is a perspective view of an improved apparatus for collecting a physiological signal of the present invention.

The present invention relates to provide an improved apparatus for collecting a physiological signal, comprising a main body, including a device for taking out the physiological signal from a finger at each side of two sides of the main body by pressing the finger therein, each device for taking out the physiological signal from a finger including: a finger contacting element, provided thereon an electrode unit for taking out an electronic signal of the physiological signal at the time of being contacted by the finger; a receiving element, provided on an upper side of the finger contacting element; and an elastic element, being connected to the receiving element, wherein via elastic force of each elastic element to open an angle at each receiving element, each finger can insert into a space between the finger contacting element and the receiving element, such that each finger could insert and engage therein.

DETAILED DESCRIPTION OF THE INVENTION

The present invention relates to provide an improved apparatus for collecting a physiological signal, comprising a main body, including two devices for taking out the physiological signal from a finger at each side of the main body by pressing the finger therein, each device for taking out the physiological signal from a finger including: a finger contacting element, provided thereon an electrode unit for taking out an electronic signal of the physiological signal at the time of being contacted by the finger; a receiving element, provided on an upper side of the finger contacting element; and an elastic element, being connected to the receiving element, wherein each elastic element is opened an angle at each receiving element according to elastic force of each elastic element, and each finger inserts into a space and engages with the finger contacting element and the receiving element.

In the present invention, the elastic element is a spring, natural rubber or synthetic rubber, but not limited to the above materials.

The term "finger" as used herein is to denote any finger.

In some embodiments, the main body is in a shape of circular arc, but not limited to this, so as to facilitate a user to hold it. An internal portion of the finger contacting element is in a sunken shape, but not limited to this. The finger contacting element and the receiving element are in a shape of circular arc, but not limited to this, so as to conform to the shape of the finger to allow the finger to engage with the device for taking out the physiological signal from a finger.

In some embodiments, an internal part of the main body includes a circuit device to be connected to the electrode unit for analyzing the physiological signal, wherein the circuit device includes an amplifier, a band-pass filter, an analogue/digital converter, and a chip for analyzing the physiological signal, for collecting, measuring and recording the physiological signal.

In some embodiments, the improved apparatus for collecting a physiological signal of the present invention further incorporates with a cloud platform, but not limited to this. The cloud platform includes a storage element for storing data of the physiological signal and proceeds as comparison and analysis of the physiological signal by the cloud platform.

In the present invention, the physiological signal is electrical cardiac signal, electromyographic signal (EMG), heart rate (HR), standard deviation (SD), low frequency (LF) that means activity of sympathetic nerve and parasympathetic nerve, high frequency (HF) that means activity of parasympathetic nerve or low-frequency power in normalized unit (LF%) that means sympathetic function, etc.

In the present invention, the main body provides at its front side a panel for displaying the data of the physiological signal of a user, and providing at its back side a battery unit for providing electric power for the improved apparatus.

In the present invention, the main body is additionally installed with a slot for being connected to a universal serial bus (UBS), wherein the UBS is connected to a computer, PDA or mobile phone, but not limited to this, and installed with the other slot for connecting to an electrode switching port electrically linked be connected to at least an electrode piece, which is attached to skin of the user for taking out the physiological signal.

The techniques, approaches and advantages of the present invention will become more apparent from the following detailed description when taken in conjunction with the accompanying drawings.

EXAMPLES

The examples below are non-limiting and are merely representative of various aspects and features of the present invention.

Figure 2:
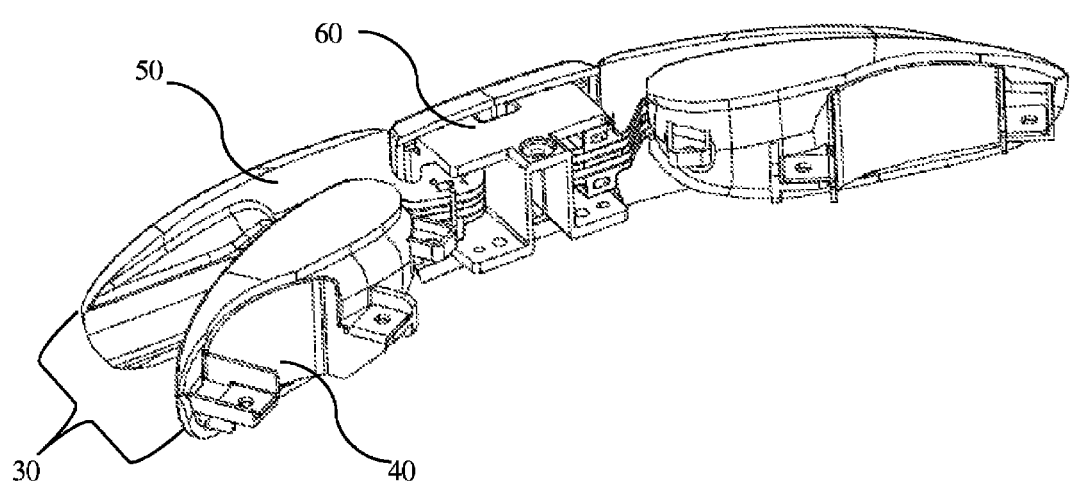
FIG. 2 is a schematic diagram of a device for taking out a physiological signal from a finger of the present invention.

As shown in FIGS. 1 and 2, an improved apparatus for collecting a physiological signal 10 of the present invention comprises a main body 20, including two devices for taking out the physiological signal from a finger 30 at each side of the main body by pressing the finger therein. Each device for taking out the physiological signal from a finger 30 includes: a finger contacting element 40, provided thereon an electrode unit 41 for taking out an electronic signal of the physiological signal at the time of being contacted by the finger; a receiving element 50, provided on an upper side of the finger contacting element 40; and an elastic element 60, being connected to the receiving element 50, wherein each elastic element 60 is opened an angle at each receiving element 50 according to elastic force of each elastic element, and each finger inserts into a space and engages with the finger contacting element 40 and the receiving element 50, such that each finger inserts and engages therein closely and finely to take out the physiological signal accurately.

Example 1

The improved apparatus for collecting a physiological signal of the present invention was capable of collecting ECG or pulse. The physiological signal was amplified in 500-1000 times by an amplifier, filtered by a 0.16-16 Hz band-pass filter, and sampled at a frequency of 256 times/sec by an analogue-digital converter included in a circuit device. After digitizing, it was immediately to proceed with analysis of heart rate variability (HRV) of a human body by using a program with respect to the physiological signal. Before sampling the physiological signal, it needed to be selected for filtering noise.

In the physiological signal, the band of a protruding portion in general was called a QRS wave, in which a point deflected upward firstly was called a Q point, a point at the top was called an R point and a point in the bottom was called an S point. In a procedure of verifying QRS, it was firstly used a peak detection procedure to find out the QRS wave in the physiological signal, and to measure parameters such as amplitude and duration from each QRS wave, and then to calculate the mean value and standard difference of each of the parameters for serving as a standard module.

Subsequently, it was to proceed with comparison with respect to each QRS wave based on such a module. If a comparison of some QRS wave showed falling outside three standard differences of the standard module, it was deemed as noise or ectopic heart and was deleted After that, an R point of a qualified QRS wave was deemed as a time point of heart beat and a time difference between the instant heart beat and a next heart beat was called an R-R interval of the instant heart beat. Later, it was to proceed with a filtering procedure of the R-R interval.

Continuously, it was to calculate the mean value and the standard difference of all R-R intervals and then to proceed with selection for all the R-R intervals. If certain R-R interval fell outside four standard differences, it was deemed as an error or unstable signal and was deleted. Then, it was to proceed with sampling and keeping value at a frequency of 7-8 Hz with respect to all qualified ECG signals so as to maintain time continuity. It was to eliminate linear deviation of the signal to avoid interference of low frequency band, and to adopt a Hamming operation to avoid mutual leakage between frequency components, respectively in a frequency spectrum. After that, it was to proceed with fast Fourier transform with respect to data of 288 seconds (2,048 points) to obtain heart rate power spectral density (HPSD), and to proceed with compensation with respect to affection resulting from sampling and Hamming operation so as to reduce error. The HDSP was quantitatively determined in power in two frequency bands via an integral way, including a low frequency (LF) power between 0.04 to 0.15 Hz and a high frequency (HF) power between 0.15 to 0.4 Hz. Meanwhile, it was to calculate quantitative parameters of a total power of high and low frequencies (TP), a ratio of the LF power and HF power (LF/HF) and a percentage of the LF power occupying the TP (LF%), in which the HF was related to activity of parasympathetic nerves of the heart, the value of LF/HF or LF% was related to activity of sympathetic nerves of the heart and Lf was considered as an integration target of functions of the sympathetic nerves and the parasympathetic nerves, i.e. an integration target of the function of autonomic nerves. The present invention provided a graphic interface, allowing the user to easily understand the examination results, while removing doubt as to whether the user had the ability of interpreting the HRV examination data.

Example 2

The improved apparatus of the present invention incorporated with a cloud platform, which integrated HRV data analysis, management and a data base. The information obtained from the apparatus was transferred to a cloud server via communication technology. Concrete suggestions for improving body conditions of the user, such as various relaxation ways of the pressure state, sport, listening to music, using volatile oil and relaxation software were obtained via calculating, analyzing and using the data in the cloud server.

The data base of the cloud platform further provided a plurality of pieces of data of clinical research for base, continuously record the long term HRV data of the user and expanded containing of the data base, while enhancing its completeness, such that the data base of the platform provided dynamic and continuity.

Example 3

According to the improved apparatus of the present invention, the main body was installed with a slot (202 or 203) for being connected to a universal serial bus (UBS), which was connected to a computer, PDA or mobile phone. The user obtained personal HRV data via connecting a wired or wireless network to a cloud platform.

Although the present invention has been explained in relation to its preferred embodiments, it is to be understood that many other possible modifications and variations can be made without departing from the scope of the invention as hereinafter claimed.

While the present invention has been described and exemplified in sufficient detail for those skilled in this art to make and use it, various alternatives, modifications, and improvements should be apparent without departing from the spirit and scope of the present invention.

One skilled in the art readily appreciates that the present invention is well adapted to carry out the objects and obtain the ends and advantages mentioned, as well as those inherent therein. The processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An improved apparatus for collecting a physiological signal, comprising a main body, being in a shape of circular arc and including two devices for taking out the physiological signal from a finger at each side of the main body, each device for taking out the physiological signal from a finger including:

a finger contacting element, being in a shape of circular arc and including thereon an electrode unit for taking out an electronic signal of the physiological signal from the finger, wherein an internal portion of the finger contacting element is in a sunken shape;

a receiving element, being in a shape of circular arc and provided on an upper side of the finger contacting element; and an elastic element, being connected to the receiving element, wherein each elastic element is adapted to open an angle at each receiving element according to elastic force of each elastic element and insertion force of each finger, allowing said each finger to easily insert into a space and engage with the finger contacting element and the receiving element.

2. The improved apparatus for collecting a physiological signal of claim 1, wherein an internal part of the main body includes a circuit device to be connected to the electrode unit for analyzing the physiological signal.

3. The improved apparatus for collecting a physiological signal of claim 1, wherein the elastic element is a spring, natural rubber or synthetic rubber.

4. The improved apparatus for collecting a physiological signal of claim 2, wherein the circuit device includes an amplifier, a band-pass filter, an analogue/digital converter, and a chip for analyzing the physiological signal.

5. The improved apparatus for collecting a physiological signal of claim 1, further comprising a cloud platform to be connected therewith, wherein the cloud platform includes a storage element for storing data of the physiological signal and proceeds with comparison and analysis as the physiological signal is transferred thereto.

6. The improved apparatus for collecting a physiological signal of claim 1, wherein the physiological signal is a heart rate variability signal.

7. The improved apparatus for collecting a physiological signal of claim 1, wherein the main body provides at its front side a panel for displaying the data of the physiological signal.

8. The improved apparatus for collecting a physiological signal of claim 1, wherein the main body provides at its back side a battery unit for providing electric power for the improved apparatus.

9. The improved apparatus for collecting a physiological signal of claim 1, wherein the main body is installed with a slot for being connected to a universal serial bus (USB).

10. The improved apparatus for collecting a physiological signal of claim 9, wherein the USB is connected to a computer, PDA or mobile phone.

11. The improved apparatus for collecting a physiological signal of claim 9, further comprising a second slot for connecting to one electrode switching port electrically linked to at least an electrode piece, which is attached to skin of a user for taking out the physiological signal.

* * * * *